United States Patent [19]
Vadgama et al.

[11] Patent Number: 6,071,739
[45] Date of Patent: Jun. 6, 2000

[54] SAMPLE ANALYZER

[75] Inventors: Pankaj M. Vadgama, Manchester; Paul H. Treloar, Cheshire, both of United Kingdom

[73] Assignee: The Victoria University of Manchester, Manchester, United Kingdom

[21] Appl. No.: 09/188,348

[22] Filed: Nov. 9, 1998

Related U.S. Application Data

[63] Continuation of application No. PCT/GB97/01296, May 12, 1997
[60] Provisional application No. 60/018,065, May 21, 1996, and provisional application No. 60/021,230, Jun. 27, 1996.

[30] Foreign Application Priority Data

May 10, 1996 [GB] United Kingdom .................. 9609736
Jun. 27, 1996 [GB] United Kingdom .................. 9613492

[51] Int. Cl.$^7$ .................................................. C12M 3/00
[52] U.S. Cl. ................................... 435/287.9; 435/287.7; 422/57; 422/61; 436/95
[58] Field of Search .............................. 422/50, 61, 68.1, 422/57; 436/95; 435/287.1, 287.9, 287.7, 288.3, 288.5

[56] References Cited

U.S. PATENT DOCUMENTS

| | | | |
|---|---|---|---|
| 5,418,136 | 5/1995 | Miller et al. | 435/5 |
| 5,582,696 | 12/1996 | Sheehan | 204/403 |

FOREIGN PATENT DOCUMENTS

| | | |
|---|---|---|
| 0 269 304 | 6/1988 | European Pat. Off. . |
| 0 447 888 | 9/1991 | European Pat. Off. . |
| 0 564 439 | 10/1993 | European Pat. Off. . |
| 295 11 566 | 1/1996 | Germany . |
| 96/30752 | 10/1996 | WIPO . |
| WO 96/30752 | 10/1996 | WIPO . |

*Primary Examiner*—David A. Redding
*Attorney, Agent, or Firm*—Nixon & Vanderhye P.C.

[57] ABSTRACT

A sample analyzer incorporates a sensor unit for providing a desired analysis of a sample. The analyzer includes a first body portion having a sensor surface (of the sensor unit) to which a sample is applied for effecting the analysis, a second body portion which is openable and closable together with said first body portion, a chamber incorporating the sensor surface when the first and second body portions are in the closed position, at least one reservoir for holding a treatment liquid and is capable of communicating with the chamber and providing a supply of treatment liquid to the chamber when the body portions are closed.

36 Claims, 8 Drawing Sheets

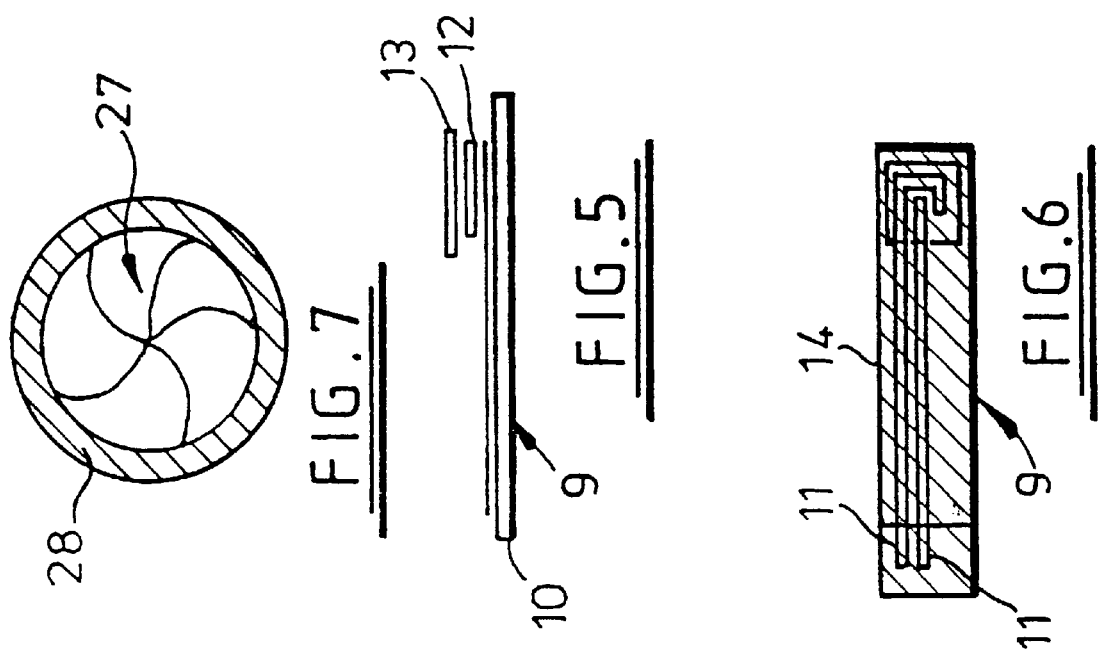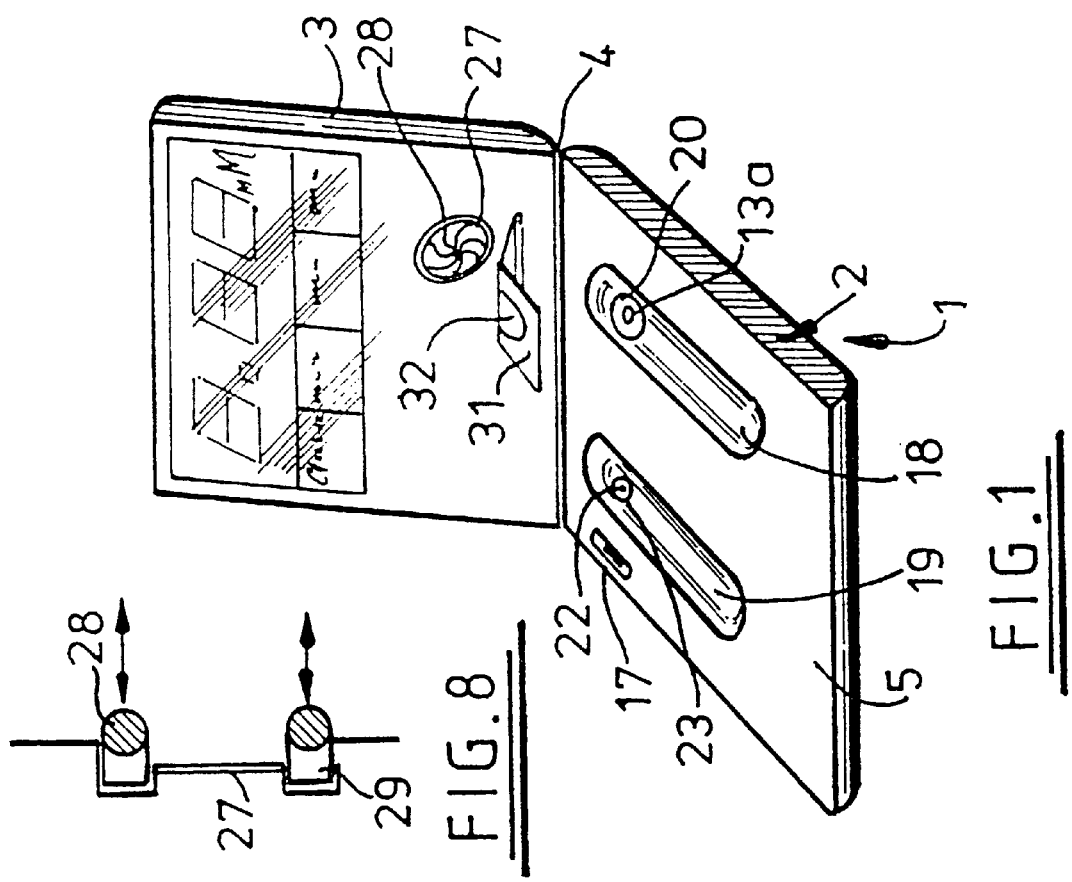

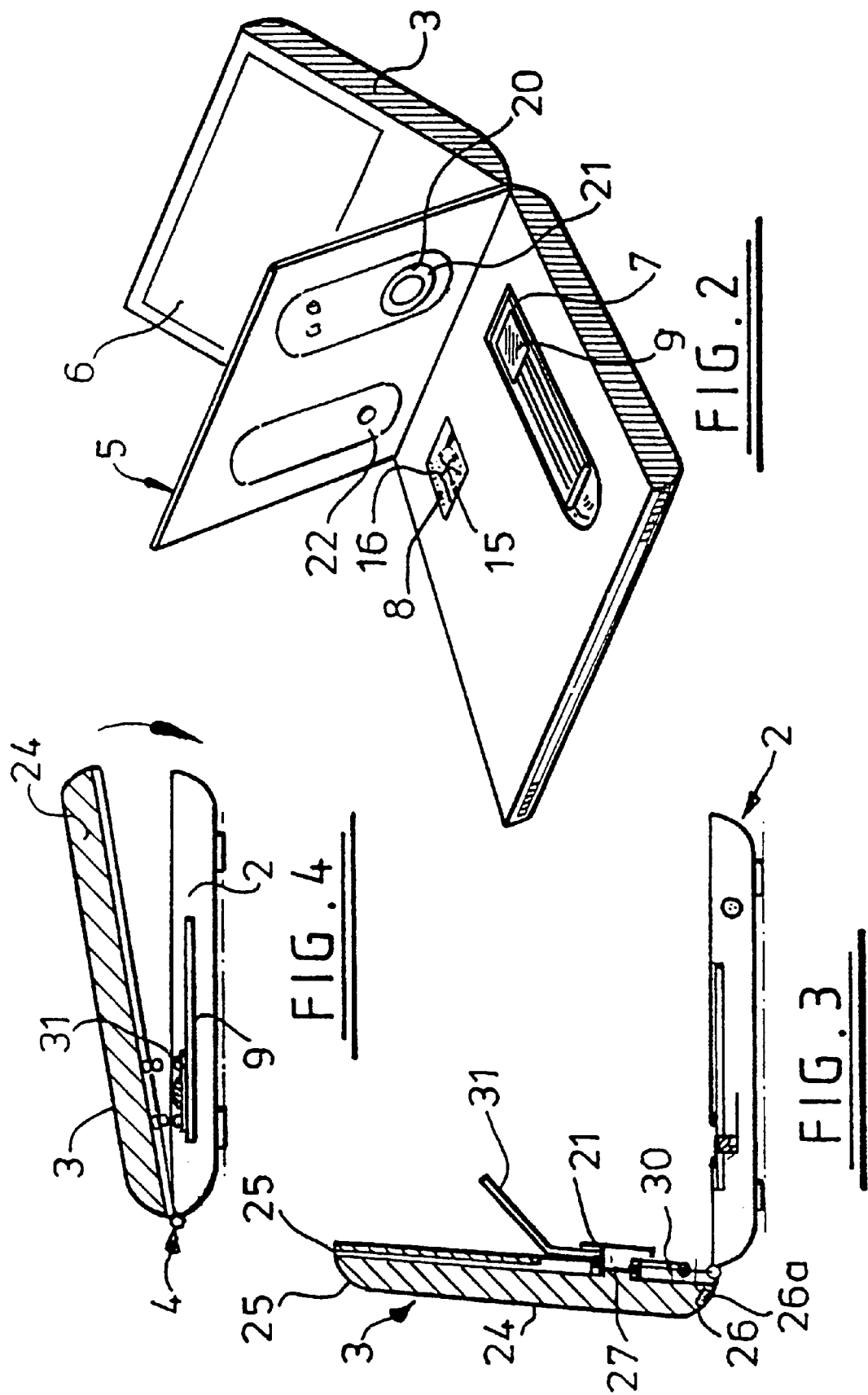

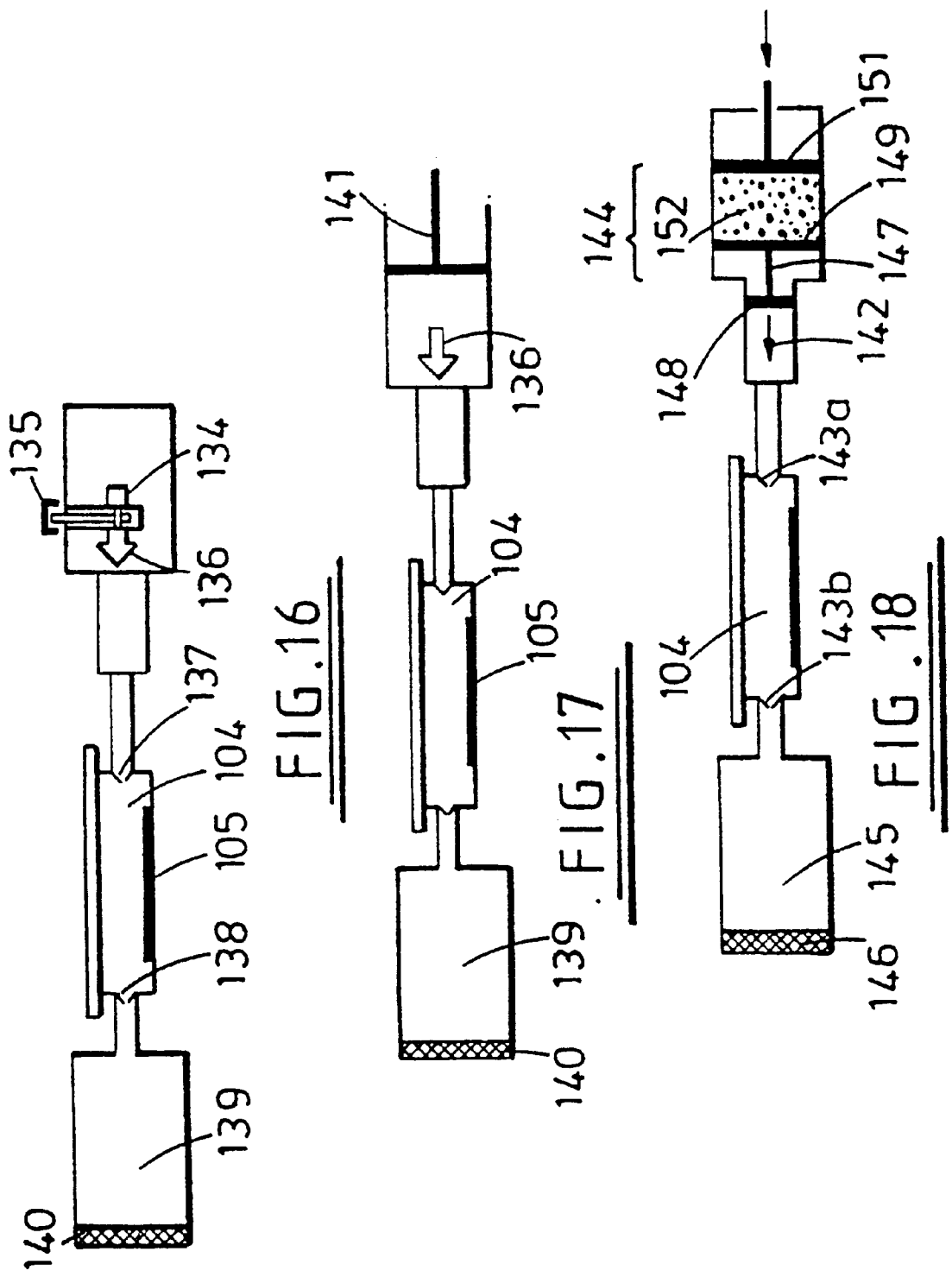

SAMPLE ANALYZER

This is a continuation of PCT/GB97/0129, filed May 12, 1997 and is also based on prior provisional U.S. applications 60/018,065 filed May 21, 1996 and 60/021,230 filed June 27, 1996.

BACKGROUND OF THE INVENTION

1. Field of the Invention

The present invention relates to a sample analyser and, more particularly. to such an analyser having a sensing surface to which a sample is applied for the purpose of effecting a desired analysis thereof.

2. Related Art

Various sensor units are known having a sensor surface to which a sample to be analysed is applied. Examples of such sensor units are of planar construction as used, for example, in the analysis of glucose levels in blood or fruit juice. Such sensors are used once and have then to be discarded. The need to use a fresh sensor for every analysis can prove expensive. Furthermore, discarded sensors which have been used for the analysis of blood may constitute a biohazard in view of the potential presence (in blood deposited on the sensor) of viruses such as HIV or hepatitis.

SUMMARY OF THE INVENTION

It is an object of the present invention to obviate or mitigate the above mentioned disadvantages.

In its broadest aspect, the present invention provides a sample analyser incorporating a sensor unit for providing a desired analysis of a sample, the analyser comprising a first body portion having a sensor surface (of the sensor unit) to which a sample is applied for effecting said analysis, a second body portion which is openable and closable together with said first body portion.

means for defining a chamber incorporating said sensor surface when the first and second body portions are in the closed position, at least one reservoir for holding a treatment liquid and being capable of communicating with said chamber and means for providing for a supply of treatment liquid to the chamber when the body portions are closed.

According to a further aspect of the present invention there is provided a sample analyser incorporating a sensor unit for providing a desired analysis of a sample, the analyser comprising a first body portion having a sensing surface (of the sensor unit) to which a sample is applied for effecting said analysis, and a second body portion incorporating a reservoir for holding a treatment liquid and having an outlet valve for discharge of treatment liquid from the reservoir.

said first and second body portions being openable and closable together such that in the closed position said valve is juxtaposed to the sensing surface to define a chamber whereby treatment liquid may be discharged from the reservoir through the valve for treating said surface.

For effecting analysis, the analyser of the invention is employed in its open configuration in which a sample may be applied to the sensing surface. The analyser has means known per se for performing an analysis on a sample applied to the sensing surface. Once the analysis has been completed, the analyser unit is "closed" so that treatment liquid may be supplied to the chamber for treatment of the sensing surface of the sensor treatment (by the treating liquid) of the sensing surface. More particularly, on closure of the analyser, a chamber is defined between the sensing surface and the valve. The valve may be opened to discharge treatment liquid from the reservoir into the chamber so as to provide for treatment of the sensor surface so that it may then be re-used for a subsequent analysis.

The treatment liquid may (for example) be one which performs any one or combination of the following functions.

(a) cleaning of the sensor surface (b) sensor regeneration (c) sterilisation of sensor surface (d) dilution and removal of sample remaining on the sensor surface.

It will be appreciated that the analyser has the advantage that the sensor unit is re-used thus avoiding the need for a fresh sensor unit for each analysis to be performed. There is a consequential advantage in that problems with disposal of used sensor units are minimised although it should be appreciated that the sensor unit used in the analyser will probably require periodic replacement. Nevertheless disposal problems (and any associated biohazard problems) are minimised.

A further advantage is that the analyser may be of simple construction so as to avoid the use of relatively complicated Flow Injection Analysis and liquidics as often employed with sensor units.

The analyser is preferably for use in analysing liquid samples (so that the sample is readily removed by the cleaning liquid) but we do not preclude the possibility of analysing in accordance with the invention being used for solid or even gaseous samples.

Conveniently, the first and second body portions are pivotally connected together so that the analyser may be of a "wallet-like" construction.

Preferably the reservoir is provided in the second body portion and its associated outlet valve are provided in the second body portion.

In one embodiment of the invention, the second body portion has an outlet valve which when the first and second body portions are closed together is juxtaposed to the sensing surface with the first and second body portions closed together the valve may be open to allow treatment liquid to come into contact with the sensing surface and "take up" into the reservoir residual sample on said surface, so that the residual sample "passes to", and becomes diluted in, the treatment liquid in the reservoir.

In this embodiment, it is preferred that the aforementioned chamber is of substantially smaller volume than the reservoir and that the analyser is maintained closed (with the valve open) for a period of time to allow the treatment liquid to be effective. This ensures that the sample taken up from the sensing surface by a treatment liquid acting as a cleaning liquid is able to disperse throughout the reservoir so as to ensure thorough cleaning of the sensing surface. It is possible to reduce this period of time by agitation (e.g. shaking) of the analyser.

Preferably the analyser is such that the valve is automatically opened as the first and second body portions are closed together and vice versa.

Preferably sealing means are provided between the juxtaposed valve and sensing surface to define a portion of the chamber. Preferably at least a portion of the sealing means is adapted to effect actuation of openings and closings of the valve on respective closing and opening of the analyser.

The valve may for example have a "shutter-type" mechanism, similar to the aperture of a camera.

In a further embodiment of the present invention, the chamber is provided with an inlet (capable of communicating with the reservoir) and a separate outlet so that treatment liquid is not returned to the reservoir. Thus the surface is always cleaned by fresh treatment liquid. This is in contrast to the abovedescribed embodiment in which the treatment liquid "takes up" residual sample from the sensing surface so that the residual sample "passes to" and becomes diluted in, the treatment liquid in reservoir.

In this embodiment of the invention, means are preferably provided for positively introducing treatment liquid in to the chamber via the inlet and/or removing treatment liquid via the outlet. These means may be pump or aerosol arrangements or the like and may be the means which provide for supply of treatment liquid (from the reservoir) to the chamber when the body portions of the device are closed together.

The inlet and outlet of the chamber are preferably associated with one-way valves so that liquid may only flow in the desired direction through the inlet and outlet.

Preferably the analyser of this embodiment has at least two reservoirs, one for holding treatment liquid (to be supplied through the inlet of the chamber) and the other serving to receive used treatment liquid from the outlet of the chamber. More preferably the analyser has at least 3 (and preferably 4) reservoirs, one of which serves to receive waste treatment liquid and the remainder of which are for containing different treatment liquids, e.g. wash, rinse or conditioning, solutions. If there are two or more reservoirs for treatment liquid then each may have a respective supply line (with associated one-way valves) running directly from the reservoir to the chamber for transfer of the respective treatment liquid to the chamber. Alternatively supply lines from the reservoirs may communicate with a multi-way selector valve from which a single line runs to the chamber.

In a further embodiment of the invention treatment liquid is removed from the chamber (via the outlet) by means providing suction at the outlet. In this embodiment there is preferably a line into the chamber from atmoshpere so that atmospheric pressure is maintained in the chamber.

The sensor unit (which may for example be a planar sensor) is preferably removably mounted in the first body portion.

Sensor units for use in the analyser are known per se.

Preferably the sensor is an electrochemical (e.g. amperometric) sensor, particularly a planar electrochemical sensor. The sensor will generally incorporate a diffusion limiting selective membrane arrangement (providing the sensing surface) which may be comprised of a single membrane or two or more membranes which together provide required properties. The membrane arrangement may have a thickness of 10 $\mu$m or more.

The sensor may be based on the use of an enzyme for determining the component of interest in the sample. The enzyme will generally be provided as a layer beneath a diffusion limiting selective membrane arrangement.

For sensors which incorporate membrane arrangements as disclosed above, the treatment liquid may serve to diffuse through the membrane and subsequently back into the "bulk phase" of the treatment liquid so as to provide for "conditioning" of the sensor.

Depending on the type of sensor unit employed, the analyser of the invention has numerous applications. e.g. medical, agricultural, and industrial (e.g. the brewing industry). Thus, for example, the analyser may be for the analysis of a component of a medical sample, e.g. glucose, ethanol, paracetamol or salicylate in blood, plasma or urine. A further example of analyser is for fructose, sucrose, malic acid, citric acid, ascorbic acid, lactic acid, tartaric acid, or ethanol in fruit juice. A still further example is for the analysis of fermentation broths in the brewing industry.

The sensor unit will be associated with electronic circuitry for determining the results of the analysis which may, for example, be shown on an in-built display device of the analyser.

A particularly preferred embodiment of analyser in accordance with the invention is for the personal use of a diabetic for the purpose of analysing a blood sample provided by a "stabbing" a finger end. Such an embodiment of analyser may incorporate a finger-shaped recess, towards one end of which is provided the sensor surface. The "stabbed" finger may be laid along the recess so that the blood contacts the sensor surface so that the blood is deposited thereon. Preferably also such an analyser also incorporates a lancet unit for piercing a finger to provide the blood sample for analysis.

The unit is particularly convenient for the personal use of a diabetic because the analyser may be of "pocket-size" construction.

Further embodiments of the invention relate to arrangement for wiping the sensor surface to remove at least a portion of residual sample therefrom. In one such embodiment the wiping means comprises an absorbent roller reciprocally moveable across the sensing surface. In a further such embodiment, the wiping means comprises a rotary device having a plurality of radial absorbent arms, the device being indexed around as necessary to draw an arm over the sensor surface to pick up residual sample. The rotary device may be provided in a replaceable cartridge.

In a further embodiment of the invention, the analyser incorporates a unit having a plurality of sensor surfaces. In this embodiment, each sensor surface will be used a certain number of times (e.g. its "allotted life") and a subsequent surface may then be used. For convenience, the sensor surface to be used at any one time is exposed through a "sensing aperture" of the device and when that surface has reached the end of its life the unit is indexed to expose a fresh sensing surface through the aperture. It will be appreciated that the unit requires less frequent replacement than would the use of individual sensor units.

BRIEF DESCRIPTION OF THE DRAWINGS

The invention will be further described by way of example only with reference to the accompanying drawings, in which:

FIG. 1 is a perspective view of one embodiment of blood analyser in accordance with the invention shown in an "open" configuration;

FIG. 2 is similar to FIG. 1 but shows the cover of the base in a raised position;

FIG. 3 is a side view of the analyser illustrated in FIG. 1

FIG. 4 is similar to FIG. 1 but showing the analyser being closed;

FIG. 5 is an exploded side view of a sensor unit as incorporated in the analyser;

FIG. 6 is a plan view of the sensor unit of FIG. 5;

FIG. 7 is a detail of a valve as employed in the analyser; and

FIG. 8 is a detail of a seal provided around the valve shown in FIG. 7.

FIGS. 16–18 schematically illustrate arrangements for delivering treatment liquid to a sensor surface.

DETAILED DESCRIPTION OF EXEMPLARY EMBODIMENTS

Figures 9, 11:
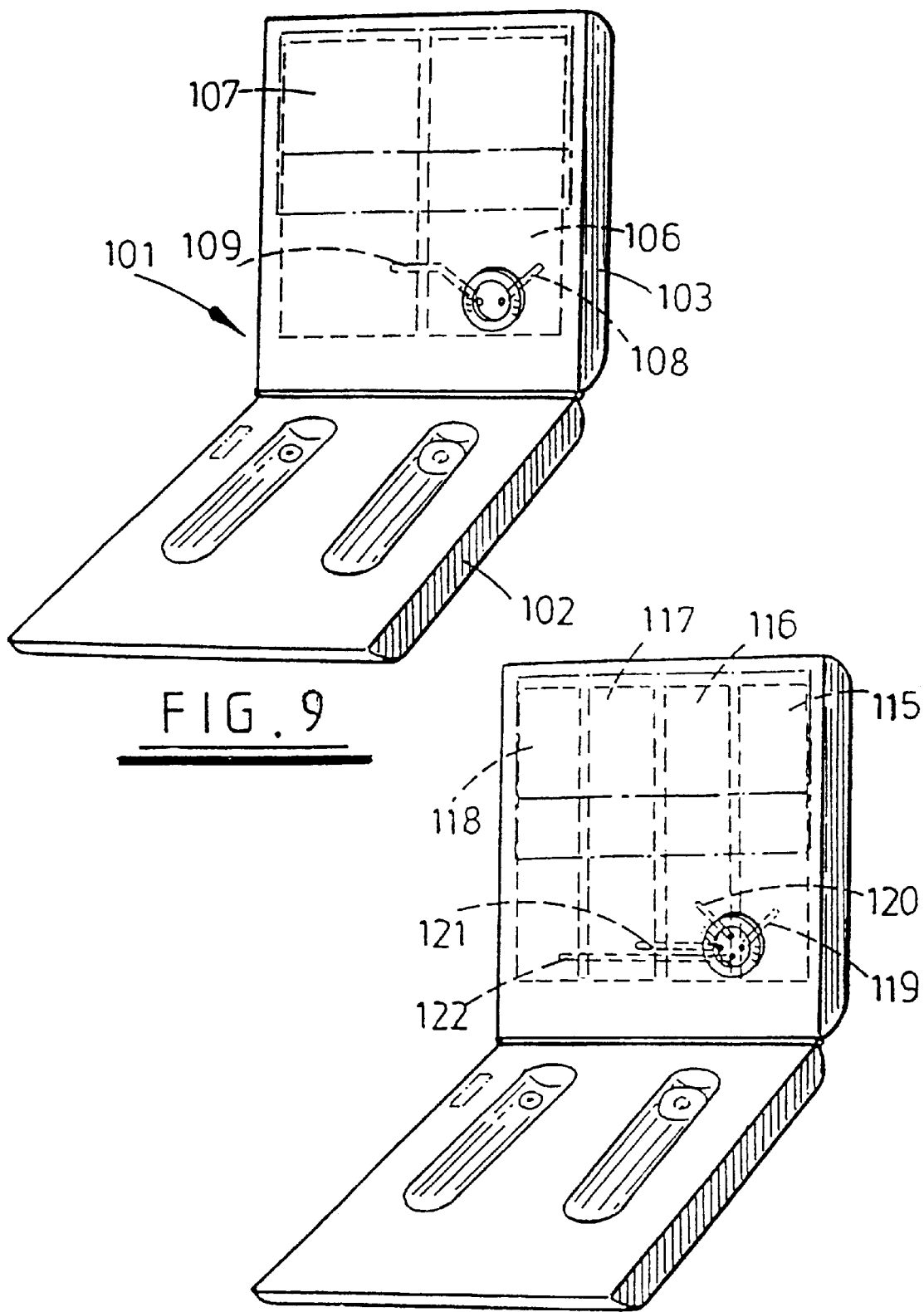
FIG. 9 illustrates a further embodiment of sample analyser in accordance with the invention.
FIG. 11 illustrates a further embodiment of sample analyser in accordance with the invention.

Referring to FIG. 1, the illustrated blood analyser 1 is an openable and closable unit comprised of a base 2 and a lid 3 which are pivotally connected together by a hinge 4 and between which is a pivotal plate-like member 5 capable of being raised from (see FIG. 2), and lowered onto (see FIG. 1), the base 2.

As will be appreciated from the subsequent description, the analyser 1 is of lightweight construction and of "pocket-size" so as to be readily portable and unobtrusive. As will also become clear, the unit is for analysing a small sample of blood (for glucose level) and displaying the result in a convenient and readily understood form of an LCD display 6 provided on the undersurface of lid 3. The sensing surface (see below) of the analyser (i.e. the surface to which a blood sample is applied) is cleaned by the treatment liquid. With these features, the analyser is eminently suitable to be carried and used by a diabetic person for the purpose of blood analysis when necessary.

A more detailed description of the construction and operation of the analyser will now be given.

Reference is made firstly to the base 2 which as seen in FIG. 2 has two recesses 7 and 8. Recess 7 is elongate and accommodates a planar glucose sensor 9, the construction of which is illustrated in FIGS. 5 and 6 Referring to these FIGS., it will be seen that sensor 9 comprises a base substrate 10 on which are laid two parallel electrode tracks 11. Towards one end of these tracks is an enzyme layer 12 which is overlaid by at least one diffusion limiting selective membrane 13. Also provided on the sensor is an insulating polymer mask 14 (not illustrated in FIG. 5) which is such as to overlay a major part of the length of tracks 11 but to leave exposed (i) those ends of the tracks remote from enzyme layer 12, and (ii) a portion (hereinafter referred to as the sensing portion 13a) of membrane 13.

Alternatively constructions of sensors may be used, e.g. sensors which do not incorporate an enzyme layer.

Electronic circuitry (not illustrated but known per se) is associated with sensor 9 for providing a reading to be displayed on the LCD display 6 and is located in the base 2 of the analyser. The circuitry may be associated with an RS232 port as illustrated in FIG. 3. Electrical connection between this circuitry and the sensor 13 may be provided via a conventional edge connector arrangement (not shown).

The other recess (i.e. recess 8) of the base 2 serves to house a replaceable lancet unit 15 having a tip 16 capable of piercing the skin of the finger. The tip 16 is intended to he moved rapidly upwards (by an actuator mechanism) to effect the piercing action. A sensor (not shown) may be provided for actuating the lancet when a finger is placed in close proximity thereto. The height to which the tip 16 is projected above the floor of recess 8 may be varied by means of a depth gauge having an adjustment knob 17.

Referring back now to FIG. 1, the plate-like member 5 is shown in its "lowered" position (i.e. on base 2) and will be seen to incorporate two elongate, parallel recesses 18 and 19 which (as described below) serve to accommodate a finger of a person using the analyser.

The recess 18 has, towards one end thereof, an aperture 20 through which the aforementioned sensing portion 13a of the membrane 13 is exposed. Furthermore, a sealing ring 21 (see FIG. 2) is provided around the aperture 20 on the undersurface of the plate-like member 5.

An aperture 22 is provided in recess 19 and the tip 16 of lancet unit 15 projects through this aperture 22. A further aperture 23 in plate-like member 15 serves to receive the adjustment knob 17 of the lancet depth gauge.

Referring, now to the lid 3 (see particularly FIGS. 3 and 4), this is of generally hollow construction so as to be capable of acting as a reservoir for a treatment liquid 24 which may be introduced into the lid 3 via a port 25 and exhausted therefrom via a port 26. Plugs 25a and 26a serve to close ports 25 and 26 thereby ensuring that the treatment liquid may be retained in the reservoir.

The undersurface of lid 3 is provided with a valve 27 surrounded by a sealing ring 28. As will be appreciated from FIG. 4 the positioning of vale 27 is such that, with the lid 3 closed, the sealing ring 28 seals around the upper peripheral edge of aperture 20.

The valve 27 is illustrated in FIG. 7 and is an electrically or mechanically actuated "shutter-type" mechanism similar to that employed in a camera. This shutter mechanism is opened and closed under the influence of movement of sealing ring 28 (as depicted in FIG. 8) by virtue of the latter being associated with a piston arrangement 29 biased outwardly of the undersurface of lid 3.

When no force is applied to sealing ring 28, it is biased outwardly of the undersurface of lid 3 by means of the piston arrangement 29. Conversely, when sealing ring 28 is pressed (from its outermost position) toward the undersurface of the lid, the piston arrangement 29 is moved to its innermost position. Electrical control circuitry (not shown) is provided such that, at its innermost position, the piston arrangement 29 serves to open valve 27. Alternatively, at its outermost position, piston arrangement serves to close valve 27.

A further feature of the lid 3 is a wiper unit 30 mounted on the undersurface thereof. This wiper unit 30 has a free, absorbent end 31 and an aperture 32. With the lid 3 closed, the wiper unit 30 is "sandwiched" between the undersurface of lid 3 and the plate-like member 5 such that aperture 32 (of the wiper unit 30) locates around the sealing ring 28. As lid 31 is opened, the absorbent end 31 (of wiper unit 31) is drawn across the sensing portion of the membrane 13.

Further opening of the lid 3 results in the wiper being returned to tile position shown in FIG. 3.

The operation of the illustrated analyser will now be described.

When a user of the apparatus requires an analysis of his or her blood to determine glucose level, the lid 3 of the analyser is initially opened. The user then positions his or her finger in close proximity to the tip 16 of the lancet unit which is then actuated so as to pierce the skin of the finger so that blood egresses therefrom. The finger is then positioned so that a sample of the blood is deposited onto the sensing portion 13a of the membrane 13. The glucose sensor 9, with its associated electronics, is able to determine the glucose concentration of the blood and the result is displayed on the LCD device 6.

The lid 2 is now closed. As a result, a chamber is, in effect, defined by the sealing rings 21 and 28 together with the sensing portion 13a (of the membrane 13) and the valve 27. Moreover, closure of the lid will have caused the sealing ring 28 to move the piston arrangement 29 against its bias thereby effecting opening of the valve 27 so that a small portion of the treatment liquid 24 is introduced into the aforementioned chamber.

Whilst the lid is maintained closed, the valve 27 remains open so that the treatment liquid is able to "take up" blood deposited on the sensing portion 13a, the blood then becoming dispersed throughout the treatment liquid 24. The sensing portion 13a thus becomes sufficiently clean for use in a subsequent analysis.

For such a subsequent analysis, the lid 3 is opened, causing the piston arrangement 29 to be moved by its biasing arrangement outwardly of the undersurface of lid 3 and thereby effecting closure of valve 27. As the lid is opened, the absorbent end 31 of the wiper unit 30 is drawn across the sensing portion 13a which is thereby dried and therefore ready for the next analysis.

It will he appreciated that the glucose sensor 9 and/or the lancet unit 15 may be replaced as required.

It is possible for the illustrated apparatus to incorporate further features and/or modifications as outlined below.

The reservoir may be provided as a removable cartridge in or on the lid 3.

The valve may be such that, on closure, there is minimal treatment liquid remaining on the sensing surface. As such, residual surface liquid is minimised or eliminated. Alternatively, the valve may such as to leave a predefined volume of treatment liquid on the sensor surface. This could be useful where the sample to be analysed requires in situ dilution before the analysis may be performed.

Although the illustrated analyser employs movement of the sealing ring 28 to actuate opening and closing of the valve, other options are possible. For example, valve opening and closing may be provided by a separate switch which is automatically actuated as necessary to effect opening and closing of the valve.

The electronic circuitry in the analyser may be such that, as the analyser is opened, a self-checking/validation procedure is performed and, on closure of the analyser, the electronic circuitry is "switched off". Furthermore, opening of the analyser may be used to commence polarisation of the sensor.

Reference is now made to the embodiment of sensor shown in FIG. 9.

The sample analyser 101 illustrated in FIG. 9 is generally similar to that shown in FIG. 1 and therefore only those points of difference will be discussed.

Figure 10:
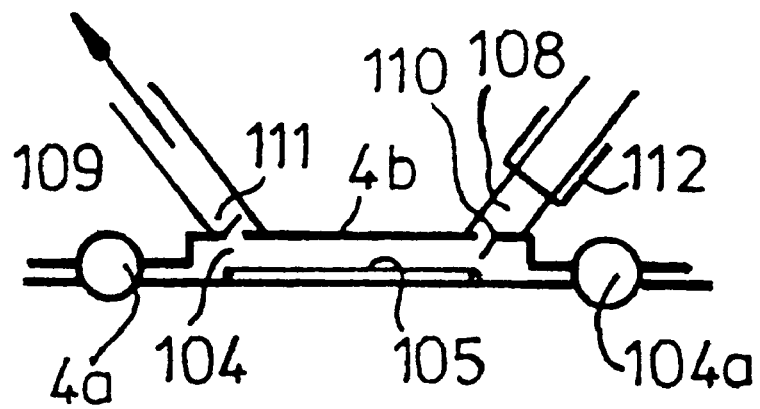
FIG. 10 is detail illustrating supply of treatment liquid from a reservoir of a sample analyser as illustrated in FIG. 9 to the sensor surface thereof.

The illustrated analyser 101 comprises a base 102 and lid 103 which are openable and closable together and which are such, in the closed position, a chamber 104 (incorporating the sensor surface 105) is formed (see also FIG. 10). This chamber is sealed by a ring 104a and is defined partly by an upper closure formation 104b.

The lid 103 is subdivided into two compartments 106 and 107 each of which is associated with a respective line 108 and 109 for providing communication between the compartment and the chamber 104. Each line 108 and 109 incorporates a respective one way valve 110 and 111. The valve 110 is such as to be openable to allow flow of liquid from compartment 106 into chamber 104 but not in the reverse direction. Conversely valve 111 is such as to be openable to allow flow of liquid from chamber 104 to compartment 107.

The line 108 is associated with a pump 112 as schematically illustrated in FIG. 10.

In use of the illustrated apparatus, compartment 106 is filled with a treatment fluid whereas compartment 107 is initially empty.

The apparatus is used for effecting an analysis of a sample (applied to the sensing surface 105) in exactly the same manner as disclosed in the aforementioned application.

Once the analysis procedure has been completed, the lid 103 is closed.

The pump 112 is then operated (under the control of the electronic circuitry of the device) so as to supply treatment liquid from the compartment 106 into the chamber 104 therefore treating the sensing surface 105. Excess liquid passes through valve 111 into compartment 107 which serves to collect the waste.

It will thus be appreciated that the sensing surface 105 is always treated with fresh treatment liquid, in contrast to the arrangement of the aforementioned application in which the treating liquid remains in the chamber to "take up" the sample into the reservoir. The amount of treatment liquid supplied to chamber 104 may be greater than the volume thereof so that the sensing surface is washed by a flow of treatment liquid.

Figure 12:
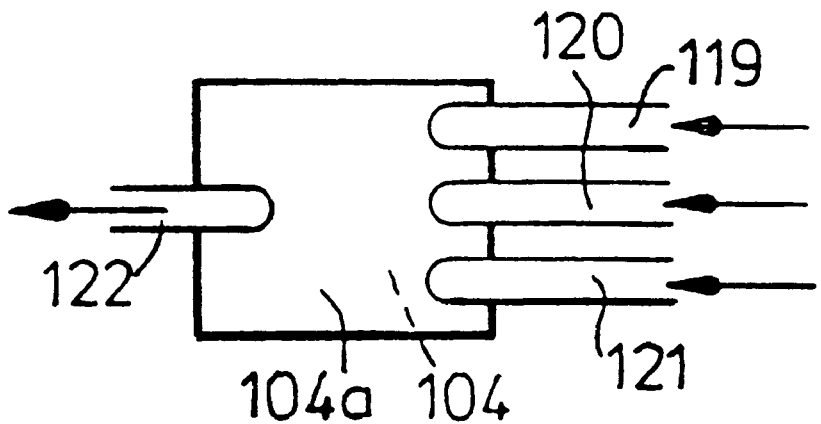
FIG. 12 illustrates one arrangement for supply of treatment liquid from the reservoir of the sample analyser of FIG. 11 to the sensor surface thereof.

Reference is now made to FIG. 11 which illustrates a modification of the sample analyser illustrated in FIG. 9 incorporates four compartments 115–118 each of which is associated with a respective line 119–122 communicating with the chamber 104 (see also FIG. 12 in which chamber 104 is viewed from above). Each of lines 119–121 is associated with a respective 1-wave valve (not shown) allowing liquid to flow from the respective to compartment 115–117 into the chamber but not in the reverse direction. Line 122 is associated with a 1-wave valve (not shown) allowing liquid to flow from chamber 104 to compartment 118 but not in the reverse direction.

In use of the device, the following solutions are held in compartments 115–117, namely:

| Compartment No. | Solution |
| --- | --- |
| 115 | Wash/Cleaning |
| 116 | Rinse |
| 117 | Storage/Conditioning |

Pumps (not shown) are provided for supplying liquid from chambers 115 to 117 to chamber 104.

Once an analysis has effected, and the lid 103 has been closed, a wash/cleaning solution is firstly supplied from compartment 115 along line 119 so as to remove the bulk of the sample on the sensor surface, the waste solution passing into line 122 for delivery to compartment 118 which serves for storage of waste. Subsequently, a rinse solution is supplied from compartment 116 along line 120 so as to rinse the sensor surface 105, the waste solution again passing to compartment 118. Finally, storage/regeneration solution is passed from compartment 117 along line 121. Excess storage/conditioning solution passes to compartment 118 but preferably at least a portion of this solution remains in chamber 104 to condition the sensor surface in readiness for the next measurement.

Figure 13:
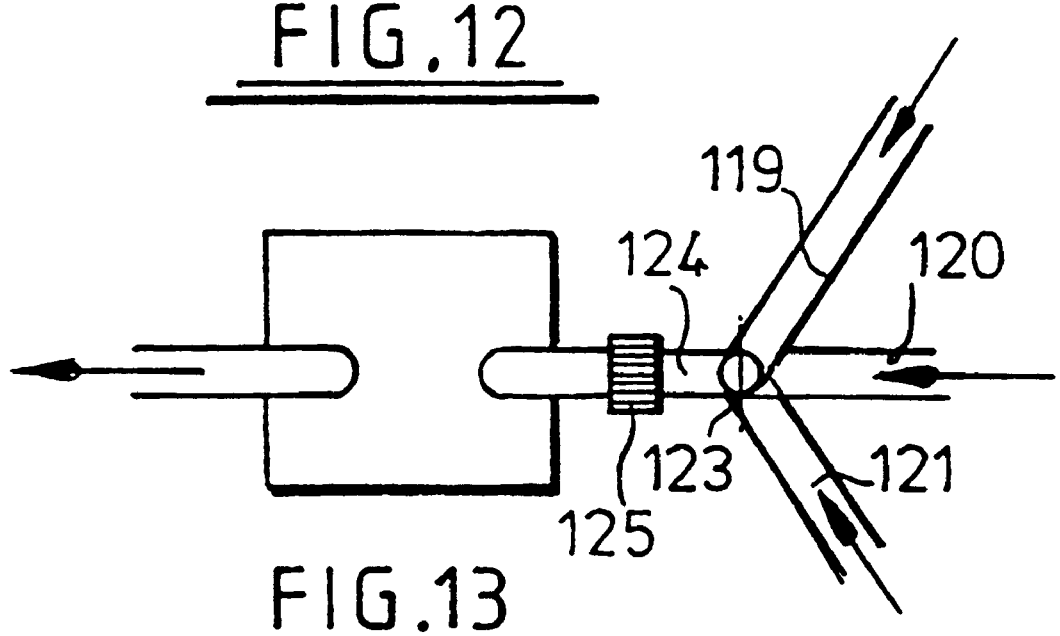
FIG. 13 is a modification of the arrangement shown in FIG. 12.

FIG. 13 is a modification of the arrangement of FIG. 12 in that the lines 119–121 (from compartments 115–117 respectively) feed to a 3-way valve 123 which communicates with chamber 104 via a line 124 in which is provided a pump 125. Line 124 also incorporates a 1-way valve (not illustrated) to permit solutions from compartments 115–117 to be supplied to chamber 104 but not in the reverse direction.

In operation of the analyse illustrated in FIG. 13 the 3-way valve is under the control of the electronic circuitry of the analyser and selectively allows communication between line 124 and any one of compartments 115–117 so that solution may be drawn therefrom as required.

Figure 14:
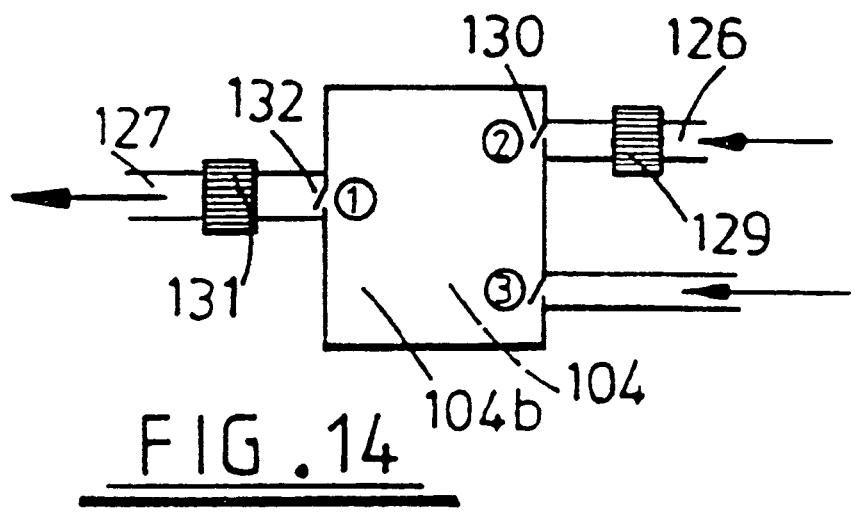
FIGS. 14 and 15 schematically illustrate an arrangement for cleaning a sensor surface of treatment liquid.
Figure 15:
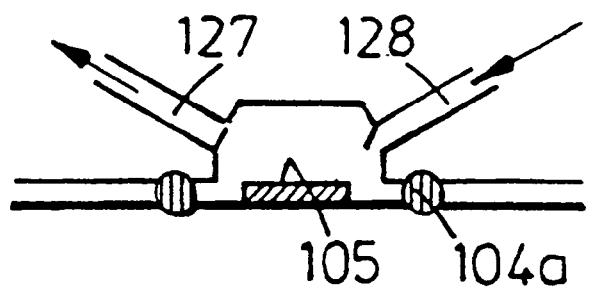

As mentioned previously, it may be desirable to leave the sensor surface 105 in contact with storage/regeneration solution between measurements made with the analyser. FIGS. 14 and 15 illustrate an arrangement which allows the regeneration/storage solution to be removed from the sensor surface prior to a measurement being made. For simplicity, the arrangement of FIG. 14 illustrates only three lines 126 to 128 communicating with the chamber 104. Line 126 communicates with a compartment containing regeneration solution and is associated with a pump 129 and a 1-way valve 130 permitting solution from line 126 to enter chamber 104. Line 127 is a waste line and is associated with a pump 131 and 1-way valve 132 permitting liquid to enter the line 131 from chamber 104. Line 128 communicates with ambient air and has a one-way valve 133 permitting air from line 128 to enter chamber 124.

In operation of the arrangement shown in FIG. 14, regeneration/storage solution is supplied along line 126 by means of pump 129 and enters chamber 104 via 1-way valve 130. Excess solution leaves the chamber 104 via 1-way valve 132 and passes to a waste-collecting compartment.

The operation of pump 129 may then be terminated to leave at least a portion of solution in contact with the sensor surface 105. Prior to the next measurement, and immediately before the lid 103 is opened, pump 131 is actuated so as to draw solution from chamber 104 into the line 127. This is permitted by virtue of 1-way valve 133 opening to allow air to enter chamber 104 via line 128.

Reference is now made to FIG. 16 which illustrates details of a mechanism for delivery of treatment solution to clean the surface of sensor 105. In the arrangement of FIG. 16, treatment solution is held in reservoir 134 which is in the form of an aerosol containing gaseous propellant and is dispensed by depression of an actuator button 135 through an aerosol nozzle (depicted schematically as 136) into chamber 104 via a one-way valve 137. Treatment liquid is able to exit chamber 104 via a one-way valve 138 so as to enter a waste reservoir 139 provided with a filter 140 which vents to atmosphere.

The arrangement of FIG. 17 is similar to that of FIG. 16 save that the propellant may be pressurised by manual or automatic actuation of a piston 141.

Reference is now made to FIG. 18 which illustrates details of a further mechanism for delivery of treatment solution to clean the surface of sensor 105. In the arrangement of FIG. 18, treatment solution is held in a reservoir 142 and is dispensed (under software control upon closure of the unit) into chamber 104 via a one-way valve 143a by means of a piston arrangement 144. Treatment liquid is able to exit chamber 104 via a one-way valve 143b so as to enter a waste reservoir 145 provided with a filter 146 which vents to atmosphere. In more detail the piston arrangement 144 comprises a "double-headed" piston 147 having one head 148 working within reservoir 142 rigidly connected to a second head 149 working within a propellant compartment 150. Also working within compartment 150 is a further piston 151. A compressible propellant 152 is provided between piston head 149 and piston 151.

The "double-headed" piston 147 is able to be selectively retained at a "primed position"0 in which the piston head 148 is in readiness for delivering treatment solution (by movement of piston head 148 to the left as viewed in FIG. 18) from reservoir 142 to chamber 105. Whilst "double headed" piston 147 is at its primed position, the propellant 152 is compressed so that when "double-headed" piston 147 is released for movement it is able to be moved (by propellant 152) to the left (as viewed in FIG. 18) to dispense treatment liquid into chamber 105. "Double headed" piston 147 is able to move only a short distance (sufficient to dispense the required amount of treatment liquid, and then retained at the position it has reached. Piston 151 is then moved to the left so as to re-compress propellant 152 so that "double headed" piston 147 is once again primed.

If the analyser employs a plurality of different treatment liquids then a single delivery arrangement of the type shown in any one FIGS. 16 to 18 may be used for delivering the treatment solutions from their respective reservoirs or each such reservoir may be provided with its own delivery arrangement.

Figure 19:
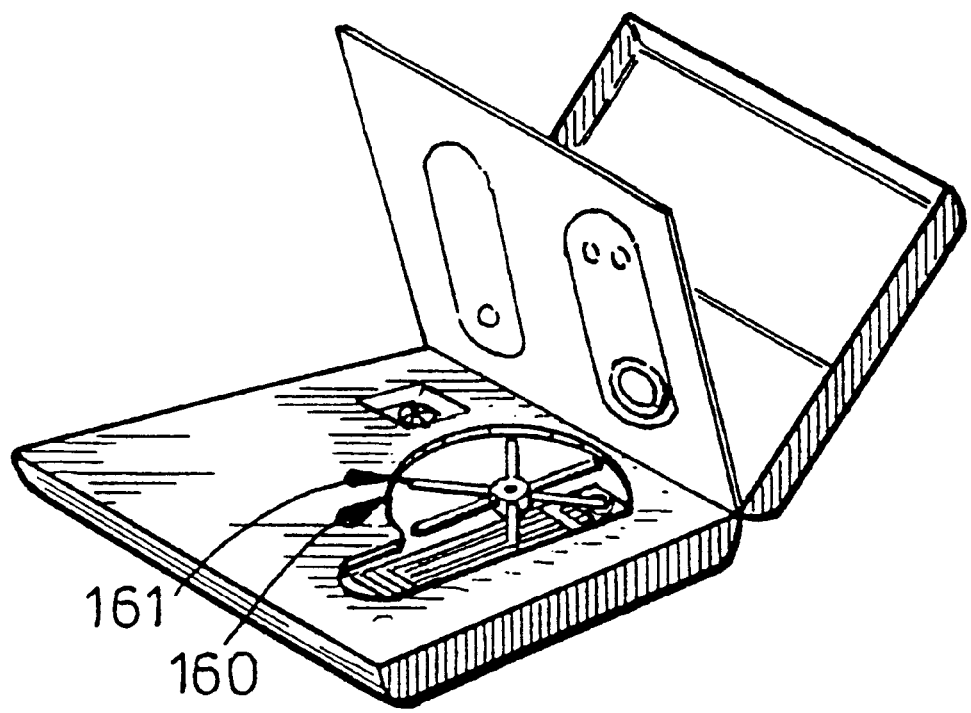
FIG. 19 illustrates a further embodiment of the invention showing the use of a plurality of wipe elements.
Figure 20A:
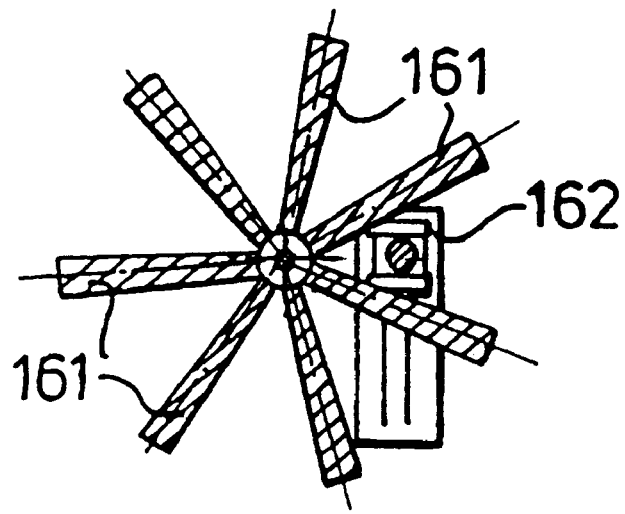
FIGS. 20a and 20b illustrate the principle of operation of the arrangement shown in FIG. 19.
Figure 20B:
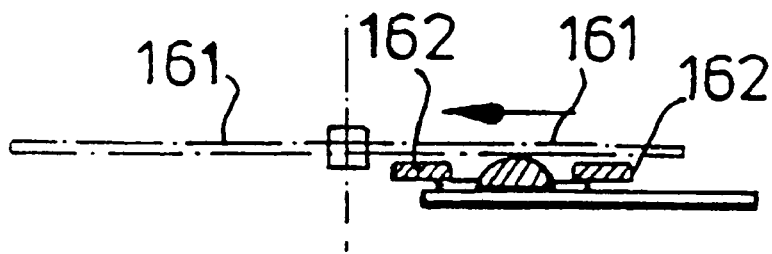

Reference is now made to FIG. 19 in which the wiper arm unit 31, 32 illustrated in FIG. 1 has been replaced by a cleaning assembly 160 comprising a plurality of radially disposed absorbent wiper units 161. After an analysis has been carried out, the unit 160 is indexed around as the lid is closed so that one of its radially wiper units 161 serves to wiper excess analyte off the sensor surface 105. Direct contact between the wiper units 161 and the sensor surface 105 may be avoided by means of spacers 162 (see also FIG. 20a and 20b).

It will be appreciated that the unit may have more than the seven wiper units illustrated. Furthermore, the unit 160 may be provided in a cartridge which may be replaced as and when all of the units 161 have been used.

Figure 22:
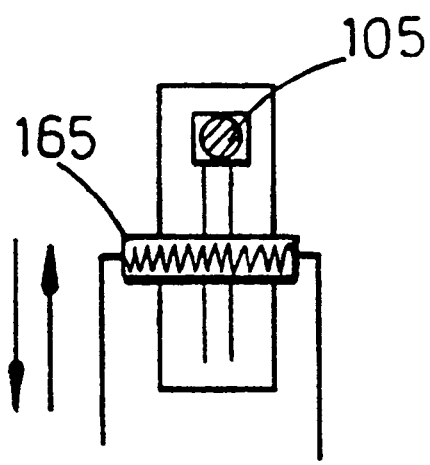
FIG. 22 illustrates the principle of operation of the arrangement shown in FIG. 20.
Figure 21:
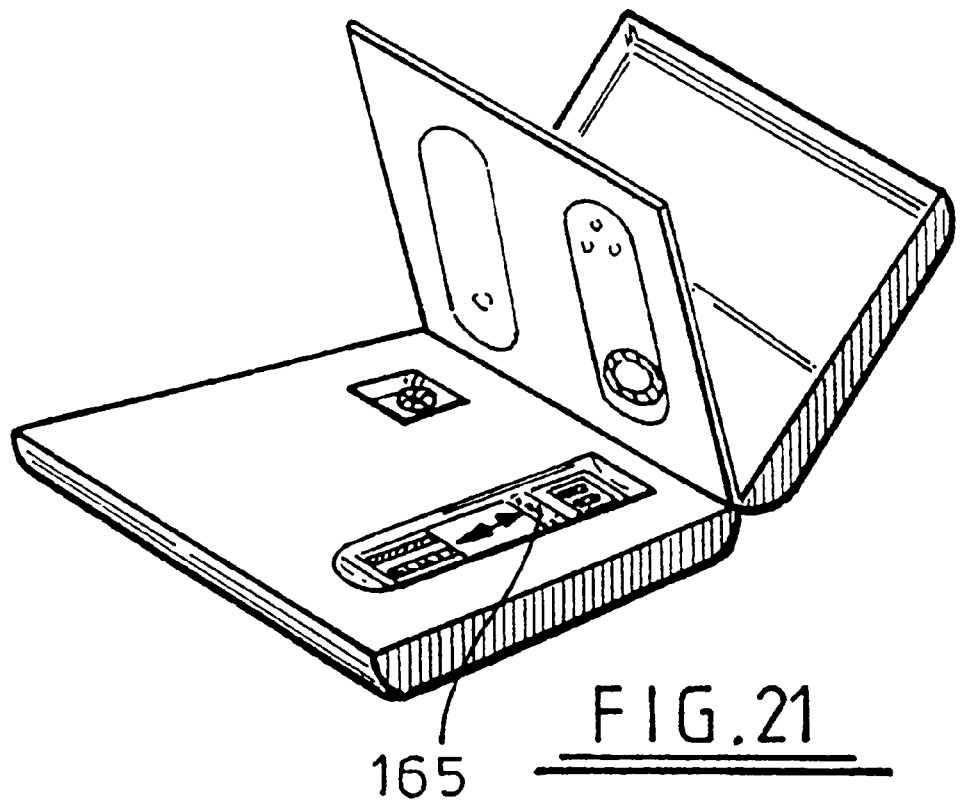
FIG. 21 illustrates a further embodiment of the invention showing the use of a roller for wiping the sensor surface.

Turning now to FIGS. 21 and 22, there is illustrated an alternative way of cleaning residual analyte from the sensor surface in which a roller 165 is employed. More particularly, as the lid is closed, the roller 165 is moved across the sensor surface prior to treatment of the latter with liquid from a reservoir of the device.

Figure 23:
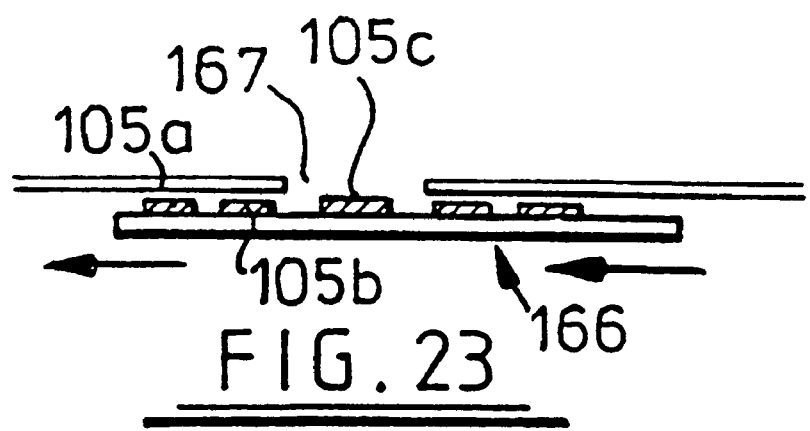
FIG. 23 illustrates a still further embodiment of analyser in accordance with the invention relating to the use of a plurality of sensor surfaces.

FIG. 23 illustrates a further embodiment of the invention in which the single sensor surface of the analyser as shown in FIG. 9 (or FIG. 1) is replaced by a unit 166 comprising a plurality of sensor surfaces 105a, 105b, 105c etc, which are consecutively exposed through a suitable opening 167 to allow application of analyte to the sensor surface. More particularly, each such sensor surface will generally be used a certain number of times before the unit is indexed forward to expose the next sensor surface to the opening 167.

It should be appreciated that the cleaning arrangements illustrated in FIGS. 19 and 21 may be employed in any embodiment of the sensor, e.g. those described with reference to FIGS. 1 to 19 or FIG. 23.

The followings features may also be employed in any of the embodiments of the invention.

1. Any reservoir to which a waste solution is passed may contain a disinfectant or bactericidal agent, particularly in the case where the analyser is to be used for blood.

2. The liquid holding compartment(s) of the analyser may be provided as replaceable cartridges. Thus, for example, wash solution may be provided in a cartridge which is simply replaced when the solution has been used. Similarly, any compartment for waste solution may also be a cartridge which is removed when full and replaced by an empty cartridge.

3. The sensor surface may be made hydrophobic, which will facilitate cleaning.

4. If the sensor needs to be polarised for measurement, it is possible for the electronic control unit of the device to maintain polarisation whilst the lid is closed. This ensures that the sensor is ready for use immediately as the lid is opened.

5. If the device incorporates a lancet (e.g. as shown in FIGS. 1 and 2) then the lancet may pass through "wiping" material impregnated with a sterilising agent.

6. The electronic control unit of the device may be programmed to provide various "user friendly" functions, e.g.

(i) step-by-step instructions relating to use of the analyser;

(ii) provide reminders as to the need to effect an analysis operation (e.g. in the case where the analyser is used by a diabetic to determine blood sugar levels). This reminder could, for example, be an audible signal;

(iii) display a reminder to change the sensor after a particular number of sensing operations;

(iv) display an instruction to replace the sensor in the case of a monitored fault therein;

(v) display a reminder about the need to replenish any solution(s) used in the analyser;

(vi) display a warning that a compartment holding waste solution is full;

Further features which may be incorporated in any of the embodiments is a communications facility of the device whereby information about an analysis, or series of analysis effected with the device may be sent via a telephone line (e.g. to a doctor).

It will be appreciate that any of the devices may also have a facility for storage of "spare parts", e.g. replacement sensors and/or replacement lancets as appropriate.

What is claimed is:

1. A sample analyser incorporating a sensor unit for providing a desired analysis of a sample, the analyser comprising:

a first body portion having a sensor surface to which a sample is applied for effecting said analysis, a second body portion which is openable and closable together with said first body portion, means for defining a chamber incorporating said sensor surface when the first and second body portions are in the closed position, at least one reservoir for holding a treatment liquid and being capable of communicating with said chamber, and means for providing for a supply of treatment liquid to the chamber when the body portions are closed, wherein the means for providing for a supply treatment liquid to the chamber comprises an outlet valve for discharge of treatment liquid from the reservoir.

2. An analyser as claimed in claim 1 wherein said chamber is of substantially smaller volume than the reservoir.

3. An analyser as claimed in claim 1 wherein the valve is automatically opened as the first and second body portions are closed together and vice versa.

4. An analyser as claimed in claim 1 wherein the reservoir is provided in the second body portion and the outlet valve associated with the reservoir is provided in the second body portion.

5. An analyser as claimed in claim 4 wherein the outlet valve is juxtaposed to the sensing surface when the first and second body portions are closed together.

6. A sample analyser incorporating a sensor unit for providing a desired analysis of a sample, the analyser comprising:

a first body portion having a sensing surface (of the sensor unit) to which a sample is applied for effecting said analysis, and a second body portion incorporating a reservoir for holding a treatment liquid and having an outlet valve for discharge of treatment liquid from the reservoir, said first and second body portions being openable and closable together such that, in the closed position, said valve is juxtaposed to the sensing surface to define a chamber whereby treatment liquid may be discharged from the reservoir through the valve for treating said surface.

7. An analyser as claimed in claim 6 wherein the volume of said chamber is substantially less than the volume of the reservoir.

8. An analyser as claimed in claim 6 wherein the valve is automatically opened as the first and second body portions are closed together and vice versa.

9. An analyser as claimed in claim 6 wherein sealing means are provided between the juxtaposed valve and sensing surface to define a portion of the chamber.

10. An analyser as claimed in claim 9 wherein at least a portion of the sealing means is adapted to effect the actuation of opening and closing of the valve on respective closing and opening of the analyser.

11. An analyser as claimed in claim 10 wherein said portion of the sealing means is biased outwardly of the undersurface of the second body portion.

12. An analyser as claimed in claim 1 wherein the chamber is provided with an inlet capable of communicating with the reservoir and a separate outlet.

13. An analyser as claimed in claim 12 provided with means for positively introducing treatment liquid into the chamber via the inlet and/or removing treatment liquid via the outlet.

14. An analyser as claimed in claim 13 wherein said means comprises a pump arrangement.

15. An analyser as claimed in claim 13 wherein said means comprises an aerosol arrangement.

16. An analyser as claimed in claim 12 wherein the inlet and outlet of the chamber are each associated with one-way valves so that liquid may only flow in the desired direction through the inlet and outlet.

17. An analyser as claimed in claim 12 having at least two reservoirs, one for holding treatment liquid and the other serving to receive used treatment liquid from the outlet of the chamber.

18. An analyser as claimed in claim 17 having at least three reservoirs, one of which serves to receive waste treatment liquid and the remainder of which are for containing different treatment liquids.

19. An analyser as claimed in claim 18 having four reservoirs.

20. An analyser as claimed in claim 18 wherein each reservoir for treatment liquid has a respective supply line with associated one-way valves running directly from the reservoir to the chamber.

21. A sample analyser as claimed in claim 18 wherein each reservoir for treatment liquid is associated with a supply line which communicates with a multi-way selector valve from which a single line runs to the chamber.

22. An analyser as claimed in claim 12 having means for providing suction at the outlet.

23. An analyser as claimed in claim 22 wherein the chamber is provided with a line from atmosphere so that atmospheric pressure is maintained in the chamber.

24. An analyser as claimed in claim 1 provided with an absorbent wiper unit which is adapted to be drawn across the sensing surface as the second body portion is opened away from the first body portion.

25. An analyser as claimed in claim 24 wherein the wiper unit comprises an absorbent roller reciprocally moveable across the sensing surface.

26. An analyser as claimed in claim 25 provided wherein the wiper unit comprises a rotary device having a plurality of radial absorbent arms, the device being indexable to draw an arm over the sensor surface.

27. An analyser as claimed in claim 26 wherein the rotary device is provided in a removable cartridge of the analyser.

28. An analyser as claimed in claim 1 wherein the sensor unit is a planar sensor.

29. An analyser as claimed in claim 28 wherein the sensor comprises a layer overlaid by at least one diffusion limiting selective membrane.

30. An analyser as claimed in claim 1 wherein the sensor unit is removably mounted in the first body portion of the analyser.

31. An analyser as claimed in claim 1 incorporating a unit having a plurality of sensor surfaces.

32. An analyser as claimed in claim 31 having a sensing aperture through which one of the sensing surfaces is exposed, and the analyser is provided with means for indexing the unit to expose a fresh sensing surface through the aperture.

33. An analyser as claimed in 1 for the analysis of blood.

34. An analyser as claimed in claim 32 provided with a lancet unit.

35. An analyser as claimed in claim 1 wherein the sensor unit is for the analysis of glucose.

36. An analyser as claimed in claim 1 wherein the first and second body portions are pivotally connected together.

* * * * *